(12) United States Patent
Ebringer

(10) Patent No.: US 6,949,348 B1
(45) Date of Patent: Sep. 27, 2005

(54) DIAGNOSIS OF SPONGIFORM DISEASES

(75) Inventor: Alan Ebringer, London (GB)

(73) Assignee: King's College London (GB)

( * ) Notice: Subject to any disclaimer, the term of this patent is extended or adjusted under 35 U.S.C. 154(b) by 0 days.

(21) Appl. No.: 09/269,607

(22) PCT Filed: Sep. 29, 1997

(86) PCT No.: PCT/GB97/02667
§ 371 (c)(1),
(2), (4) Date: Feb. 20, 2003

(87) PCT Pub. No.: WO98/13694
PCT Pub. Date: Apr. 2, 1998

(30) Foreign Application Priority Data

Sep. 27, 1996 (GB) .............................................. 9620195

(51) Int. Cl.[7] ...................... G01N 33/53; G01N 33/554; G01N 33/567
(52) U.S. Cl. ........................ 435/7.2; 435/7.32; 435/975
(58) Field of Search ................................ 435/7.2, 7.32, 435/975, 5, 327, 4, 243; 530/300; 424/130.1, 164.1, 184.1, 185.1, 234.1

(56) References Cited

U.S. PATENT DOCUMENTS 4,038,143 A * 7/1977 Juni ............................. 435/37

OTHER PUBLICATIONS

Eylar, E. H., et al., "Experimental Allergic Encephalomyelitis: Synthesis of Disease–Inducing Site of the Basic Protein"*Science*, Jun. 1970, vol. 168, No. 3936, pp 1220–1223.

Chemical Abstracts, vol. 80, No. 11, Mar. 18, 1974, Columbus, Ohio, US; abstract No. 56313, A. Wajgt.: "Assessment by immunofluorescence methods of humoral antimyelin antibody in rats with cyanide encephalopathy." p. 68, col. 1, XP002052988, and Ann. Immunol. (Poznan), vol. 5, No. 1–2, 1973, pp. 51–58.

B.H. Toh et al.: "The 200– and 150–kDA neurofilament proteins react with 1gG autoantibodies from patients with kuru, Creutzfeldt–Jakob disease, and other neurologic diseases." Proceedings of the National Academy of Sciences of USA., vol. 82, May 1985, Washington, US, pp. 3485–3489, XP002052986.

R.L. Sidman et al.: "Transmissible spongiform encephalopathy in the gray tremor mutant mouse." Proceedings of the National Academy of Sciences of USA., vol. 82, Jan. 1985, Washington US, pp. 253–257, XPOO2052987.

Chemical Abstracts, vol. 109, No. 21, Nov. 21, 1988, Columbus, Ohio, US, abstract No. 187890, M. P. McKinley, et al.: "Developmental regulation of prion protein mRNA in brain."p. 484; col. 2; and CIBA Found. Symp., vol. 135 (Novel Infect. Agents Cent. Nerv. Syst.), 1988, pp. 101–116.

* cited by examiner

*Primary Examiner*—Mark Navarro
(74) *Attorney, Agent, or Firm*—Joseph T. Leone, Esq.; DeWitt Ross & Stevens S.C.

(57) ABSTRACT

A diagnostic test is provided for spongiform encephalopathy and other demyelinating conditions in mammals which comprises assaying antibodies present in the mammal which bind to an antigenic peptide which exhibits molecular mimicry of a mammalian myelin peptide, e.g. one having the sequence FSWGAEGQK. This test is useful for detecting BSE in cattle by assaying sera collected from the cattle for antibodies to a species of *Acinetobacter, Agrobacterium* or *Ruminococcus*, or a peptide having a sequence present in the species which mimics a peptide of bovine myelin and identifying animals having a level of antibodies at least about two standard deviations above that of healthy control animals.

27 Claims, 1 Drawing Sheet

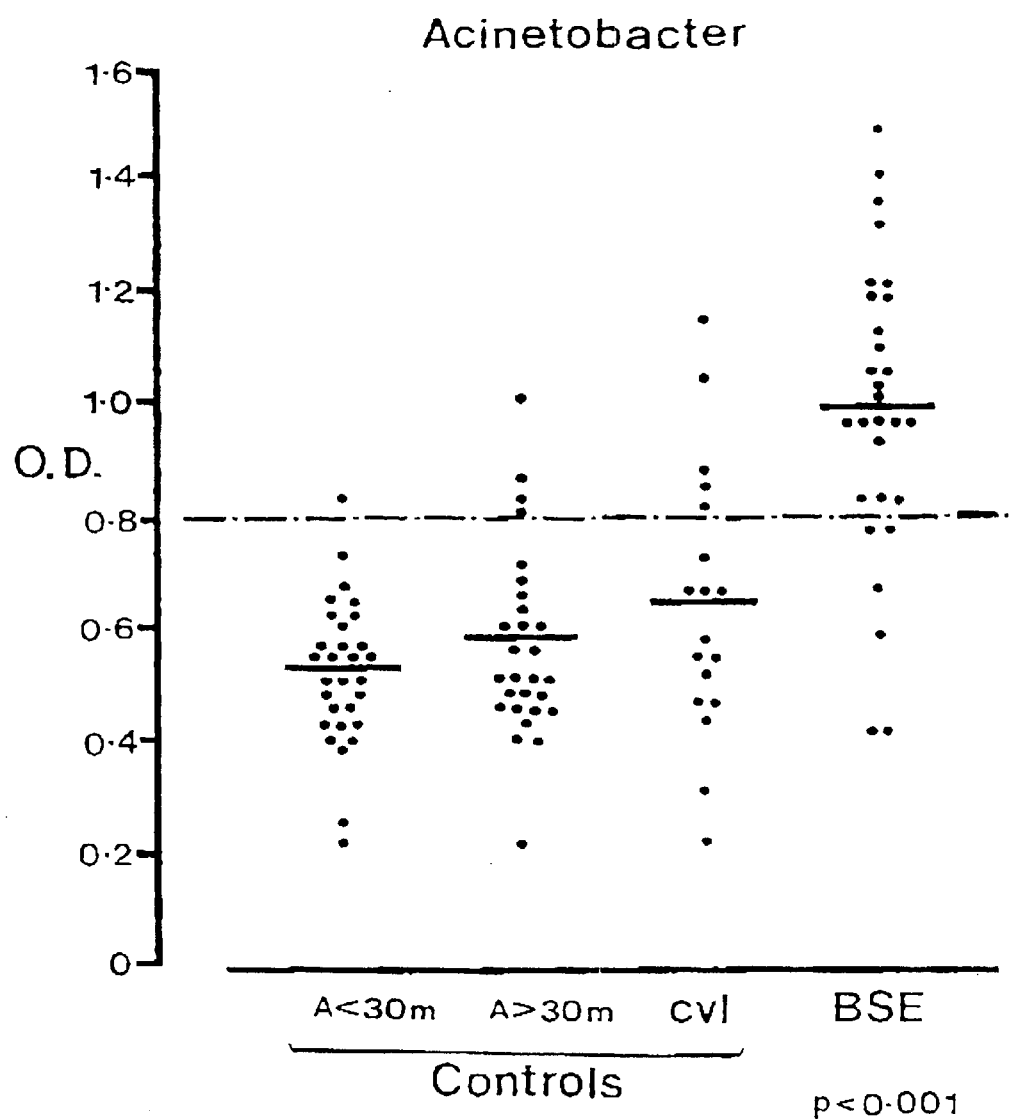

DIAGNOSIS OF SPONGIFORM DISEASES

This invention relates to the detection of spongiform encephalopathy and other demyelinating conditions in mammals and is particularly, but not exclusively, concerned with the diagnosis of bovine spongiform encephalopathy (BSE).

BSE is a recent neurological disorder of cattle, which was first reported in the U.K. after 1982 following a change in the preparation of "bone and meal" feeds. BSE has attracted some public concern, lest it be transmitted to humans following meat consumption. It has been suggested that BSE is caused by "prions", a type of infectious protein.

The present invention is based on an alternative model of the genesis of various forms of spongiform encephalopathy and other demyelinating conditions in mammals. According to the proposed model. BSE and related diseases are conceived as autoimmune diseases arising as a result of molecular mimicry between certain infective agents and the myelin of the infected mammal. This new model of BSE, in particular, is based on the following experimental observations.

A characteristic histopathological feature of BSE is a "spongiform" appearance, which also occurs in chronic but not acute "experimental allergic encephalomyelitis" (EAE), at least in rabbits and guinea pigs. A short sequence of bovine myelin (FSWGAEGQK) (SEQ. ID. NO: 1), which withstands denaturation following heating to 100° C. for one hour, was reported over twenty-five years ago to produce hind quarters paralysis, tremors and death, following inoculation into guinea pigs, which to some extent resembles the features observed in cattle suffering from BSE. In accordance with the present invention, this sequence has been used as a computer probe to search for proteins showing molecular mimicry. This sequence, in denatured form, may be described as encephalitogenic.

Analysis of proteins in databases (Genbank and SwissProt) revealed that 3 microbes showed molecular mimicry of the bovine myelin sequence, the best one being found in 4-carboxy-muconolatone-decarboxylase of *Acinetobacter calcoaceticus*, a common microbe present in soil and water supplies. These sequence similarities are shown in the following Table.

Comparison of Amino Acids of Bovine Myelin to Microorganisms from GenBank and SwissProt Which Have Similar Sequences in Other Proteins.

ies present in the mammal which bind to an antigenic peptide which exhibits molecular mimicry of a mammalian myelin peptide, especially one having the sequence FSWGAEGQK (SEQ. ID. NO: 1). The term "molecular mimicry" refers to a degree of similarity (sequence homology) as between the antigenic peptide and a myelin peptide which results in the formation of antibodies which cross-react with myelin and demyelinate nervous tissue. The presence of such antibodies at elevated levels compared to those found in unaffected animals is therefore a marker for BSE which may be used to detect BSE at an early stage at which curative or other appropriate action may be taken.

The assay may be carried out using the whole *Acinetobacter* or other organism as the test antigen. Any strain of *Acinetobacter* having the antigenic peptide identified above may be used. Alternatively the isolated peptide or a synthetic form of the peptide may be used as antigen. Any suitable type of assay procedure may be used, the ELISA method being especially convenient.

Antibody levels indicative of BSE are those which are significantly higher than the control levels. Usually, levels elevated to about 2 standard deviations above the controls may be taken as a positive indication but margins around figure may be possible or desirable for purposes of caution.

Procedures for carrying out an assay in accordance with this invention are described in the following illustrative Example, based on comparison of sera from animals known to have had BSE with sera from healthy animals.

BRIEF DESCRIPTION OF THE DRAWING FIGURE

The sole drawing FIGURE is a graph depicting *Acinetobacter calcoaceticus* antibody titres for four groups of animals: three control groups known not to have BSE and one group known to have BSE.

MATERIALS AND METHODS

Bovine Sera

Sera from 29 animals, which were found at post-mortem to satisfy the criteria of BSE and 18 animals which did not, were supplied by the Central Veterinary Laboratory (CVL) (New Haw, Addlestone. Surrey), an executive agency of he U.K. Ministry of Agriculture, Fisheries and Food (MAFF). The 18 animals which did not have BSE had been referred to CVL because of abnormal behaviour but post-mortem examinations carried out by MAFF had included BSE.

Comparison of Amino Acids of Bovine Myelin to Microorganisms from GenBank and SwissProt Which Have Similar Sequences in Other Proteins.

| Source | Amino Acids | Positions | Locations |
| --- | --- | --- | --- |
| Bovine myelin | LSRFSWGAE (SEQ. ID. NO: 2) | 110–118 | |
| Acinetobacter calcoaceticus | ISRFAWGEV (SEQ. ID. NO: 3) | 41–49 | 4-carboxy-mucolactone decarboxylase |
| Agrobacter tumefaciens | YTRFTWGAP (SEQ. ID. NO: 4) | 693–701 | β-glucosidase |
| Ruminococcus albus | YTQFEISAE (SEQ. ID. NO: 5) | 274–282 | β-glucosidase |

Alphabetic letters refer to biochemical symbols for amino acids.

In conformity with the new model, it has now been found that sera of BSE affected cattle contain significantly high levels of antibodies to *Acinetobacter* species.

The present invention therefore provides a diagnostic test for spongiform encephalopathy and other demyelinating conditions in mammals which comprises assaying antibod- Furthermore, 30 sera from animals aged less than 30 months (A<30M) (8 Friesians, 21 Hereford-Friesian and 1 Charolais-Friesian crossbreeds) and 28 sera from animals aged more than 30 months (A>30M) (all dairy Friesians), were used as further controls. These were collected from a farm, kept under "organic farming" conditions where no case of BSE had been reported. Serum samples were obtained during routine herd testing.

Preparation of Bacteria

*Acinetobacter calcoaceticus* was obtained from The National Collection of Industrial and Marine Bacteria Ltd. NCIMB 10694 (Aberdeen). Cultures were grow in 21 flasks on an orbital shaker for 2 days at 30° C., in 200 ml nutrient broth (Oxoid; 25 g/l). Flasks were inoculated with 10 ml of the corresponding starter culture left shaking at 37° C. for 6 hours. Batch culture cells were harvested by centrifugation at 6000 r.p.m. for 20 minutes at 4° C. (MSE 18.6×250 ml rotor). The pellets of cells were then washed three times with 0.15 M phosphate-buffered saline (PBS; pH 7.4) before being finally resuspended in 20 ml of PBS. A stock solution of the suspension was prepared by diluting in 0.05 M carbonate buffer (pH 9.6) to give an optical density (OD) reading of 0.25 on the spectrophotometer (Corning Model 258).

Enzyme-linked Immunosorbent Assay

ELISA assays were carried out in the conventional manner. Briefly ELISA plates were coated with bacteria overnight at 4° C. and the non-specific Sites blocked with PBS containing 1% Tween. 0.2% ovalbumin (Sigma. Grade III), plates washed and a 1/200 dilution of test or control serum added. The plates were incubated at 37° C. for 1 hour, washed and rabbit anti-cow immunoglobulin (IgG+IgA+IgM) (1:400) (Dako Ltd.) added. The plates were reincubated for 2 hours, washed and substrate added. The reaction was stopped with a 2 mg/ml solution of sodium fluoride (Sigma). The plates were read at 630 nm on a microtitre plate reader (Dynatech MR 600) and results expressed as OD ±S.E. All studies were carried out under code in that the tester did not know which were test or control sera. The mean OD units of total immunoglobulin antibodies in different groups were compared using Student's t-test.

Elisa Method Sheet

1. Dilute antigen in coating buffer, add 200 µl to each well. Incubate overnight at 4° C. wrapped in foil.
2. Wash out the antigen, using washing/incubation buffer; the wells of the tray should be completely full during the washing stages as the Tweeu-20 prevents any further protein from being absorbed onto the plastic. Wash 3 times, leaving for approx. 4 minute intervals at room temperature.
3. Incubate the plate at 37° C. for 1 hr with 0.2% Ovalbumin in washing/incubation buffer.
4. Add 200 µl of test serum. Dilutions are made in washing/incubation buffer. Incubate for 2 hours at 37° C. wrapped in foil.
5. Repeat washing process as in 2.
6. Add 200 µl Horseradish peroxide HRP-conjugated second antibody, also diluted in washing/incubation buffer.
7. Repeat washing process as in 2.
8. Add 200 µl substrate (ABTS) to wells; leave to develop colour for approx. 20 minutes in the dark at room temperature. Stop reaction with 100 µl of stopping solution and read plate at 630 nm.

Results

Antibodies to *A. calcoaceticus* of total immunoglobulin (IgG–IgA+IgM) were significantly elevated in the BSE sera (mean±SE:0.99=0.05) when compared to CVL controls (0.65±0.06) (t=4.48, p<0.001), organic farming controls aged more than 30 months (0.57±0.03) (t=7.19, p<0.001) and organic farming controls aged less than 30 months (0.53±0.02) (t=8.64, p<0.001). These results are shown in the attached Figure.

Legend to Figure:

Antibody titres (bar=mean) for 30 controls aged less than 30 months (A<30 m), 28 controls aged more than 30 months (A>30 m), 18 controls from the Central Veterinary Laboratory (CVL) compared to 29 BSE sera, when tested against *Acinetobacter calcoaceticus* (FIG. 1a) and *E. coli* (FIG. 1b). (Dashed line represents 95% confidence limits for mean of controls: A<30 m +A>30 m –one tailed test) (OD=optical density).

There was no significant difference between the CVL controls and the organic farming controls aged more than 30 months, but there was a small, statistically significant difference with the sera from animals aged less than 30 months (t=2.41, p<0.05). A re-examination of the CSL control serum with the highest anti-*Acinetobacter* level of 1.16 OD, showed that it came from a clinically normal control animal, diagnosed as negative to BSE on the statutory diagnostic criteria, and it was also uegative when tested for scrapie associated fibrils. This case did however have white matter vacuolation of the substantia nigra and internal capsule, although this had been seen before and not considered significant.

One clear result from these studies, is that in at least in one "transmissible spongiform encephalopathy" (TSE), namely BSE, a specific immune response can be demonstrated against a microbe that is found readily in the environment of cattle and which also happens to possess a molecular sequence resembling bovine myelin.

Other forms of spongiform encephalopathy including Creuzfeld Jacob disease (CJD) and Multiple Sclerosis (MS) are open to explanation on the same model as indicated for BSE. CJD sera and MS sera are currently under test to confirm the presence of cross-reacting antibodies.

What is claimed is:

1. A method of diagnosing spongiform encephalopathy in a mammalian subject, including a human subject, the method comprising measuring a bodily fluid of the subject for antibodies capable of binding to a microorganism classified within a genus selected from the group consisting of *Acinetobacter, Agrobacter*, and *Ruminococcus*, and wherein the microorganism contains an antigenic peptide that has sufficient sequence homology with a mammalian myelin peptide such that the antibodies capable of binding to the microorganism are cross-reactive with mammalian myelin and demyelinate nervous tissue, wherein an elevated level of the antibodies in the subject as compared to a corresponding level of the antibodies in known unaffected subjects indicates spongiform encephalopathy in the subject.

2. The method of claim 1, wherein the mammalian subject is a bovine, and the method is to diagnose bovine spongiform encephalopathy.

3. The method of claim 1, wherein the bodily fluid measured is serum.

4. The method of claim 1, wherein the bodily fluid is measured for the presence of antibodies capable of binding to a microorganism classified within the genus *Acinetobacter*.

5. The method of claim 1, wherein the bodily fluid is measured for the presence of antibodies capable of binding to a microorganism classified within the genus *Agrobacter*.

6. The method of claim 1, wherein the bodily fluid is measured for the presence of antibodies capable of binding to a microorganism classified within the genus *Ruminococcus*.

7. The method of claim 1, wherein the bodily fluid is measured for the presence of antibodies capable of binding to a microorganism selected from the group consisting of *Acinetobacter calcoaceticus, Agrobacter tumefaciens*, and *Ruminococcus albus*.

8. The method of claim 1, wherein the antibodies are measured using an enzyme-linked immunosorbent assay.

9. The method of claim 8, wherein the enzyme-linked immunosorbent assay utilizes as a test antigen whole bacteria classified within a genus selected from the group consisting of *Acinetobacter, Agrobacter*, and *Ruminococcus*.

10. The method of claim 8, wherein the enzyme-linked immunosorbent assay utilizes as a test antigen whole bacteria selected from the group consisting of *Acinetobacter calcoaceticus, Agrobacter tumefaciens*, and *Ruminococcus albus*.

11. The method of claim 8, wherein the enzyme-linked immunosorbent assay utilizes as a test antigen whole *Acinetobacter calcoaceticus* bacteria.

12. The method of claim 8, wherein the enzyme-linked immunosorbent assay utilizes as a test antigen whole bacteria wherein the bacteria contains an antigenic peptide comprising an amino acid sequence as shown in SEQ. ID. NOS: 1, 3, 4, and 5.

13. The method of claim 1, wherein the antibodies are measured using an enzyme-linked immunosorbent assay that utilizes as a test antigen a polypeptide selected from the group consisting of SEQ. ID. NOS: 1, 3, 4, and 5.

14. The method of claim 1, wherein the microorganism contains an antigenic peptide comprising an amino acid sequence as shown in SEQ. ID. NOS: 1, 3, 4, and 5.

15. A method of diagnosing spongiform encephalopathy in a bovine subject, the method comprising measuring serum collected from a bovine subject for antibodies capable of binding to a microorganism classified within a genus selected from the group consisting of *Acinetobacter, Agrobacter*, and *Ruminococcus*, and wherein the microorganism contains an antigenic peptide that has sufficient sequence homology with a mammalian myelin peptide such that the antibodies capable of binding to the microorganism are cross-reactive with mammalian myelin and demyelinate nervous tissue, wherein an elevated level of the antibodies in the subject as compared to a corresponding level of the antibodies in known unaffected subjects indicates spongiform encephalopathy in the subject.

16. The method of claim 15, wherein the bodily fluid is measured for the presence of antibodies capable of binding to a microorganism classified within the genus *Acinetobacter.*

17. The method of claim 15, wherein the bodily fluid is measured for the presence of antibodies capable of binding to a microorganism classified within the genus *Agrobacter.*

18. The method of claim 15, wherein the bodily fluid is measured for the presence of antibodies capable of binding to a microorganism classified within the genus *Ruminococcus.*

19. The method of claim 15, wherein the bodily fluid is measured for the presence of antibodies capable of binding to a microorganism selected from the group consisting of *Acinetobacter calcoaceticus, Agrobacter tumefaciens*, and *Ruminococcus albus.*

20. The method of claim 15, wherein the antibodies are measured using an enzyme-linked immunosorbent assay.

21. The method of claim 20, wherein the enzyme-linked immunosorbent assay utilizes as a test antigen whole bacteria classified within a genus selected from the group consisting of *Acinetobacter, Agrobacter*, and *Ruminococcus.*

22. The method of claim 20, wherein the enzyme-linked immunosorbent assay utilizes as a test antigen whole bacteria selected from the group consisting of *Acinetobacter calcoaceticus, Agrobacter tumefaciens*, and *Ruminococcus albus.*

23. The method of claim 20, wherein the enzyme-linked immunosorbent assay utilizes as a test antigen whole *Acinetobacter calcoaceticus* bacteria.

24. The method of claim 20, wherein the enzyme-linked immunosorbent assay utilizes as a test antigen whole bacteria wherein the bacteria contains an antigenic peptide comprising an amino acid sequence as shown in SEQ. ID. NOS: 1, 3, 4, and 5.

25. The method of claim 15, wherein the antibodies are measured using an enzyme-linked immunosorbent assay that utilizes as a test antigen a polypeptide selected from the group consisting of SEQ. ID. NOS: 1, 3, 4, and 5.

26. The method of claim 15, wherein the microorganism contains an antigenic peptide comprising an amino acid sequence as shown in SEQ. ID. NOS: 1, 3, 4, and 5.

27. A kit for diagnosing spongiform encephalopathy in a mammalian subject, including a human subject, the kit comprising, in combination:

a first vessel containing a microorganism classified within a genus selected from the group consisting of *Acinetobacter, Agrobacter*, and *Ruminococcus*, wherein the microorganism contains an antigenic peptide comprising an amino acid sequence as shown in SEQ. ID. NOS: 1, 3, 4, and 5; and instructions for use of the kit.

* * * * *

SEQUENCE LISTING

```
<160> NUMBER OF SEQ ID NOS: 5

<210> SEQ ID NO 1
<211> LENGTH: 9
<212> TYPE: PRT
<213> ORGANISM: Bos sp.

<400> SEQUENCE: 1

Phe Ser Trp Gly Ala Glu Gly Gln Lys
1               5
```

```
<210> SEQ ID NO 2
<211> LENGTH: 9
<212> TYPE: PRT
<213> ORGANISM: Bos sp.

<400> SEQUENCE: 2

Leu Ser Arg Phe Ser Trp Gly Ala Glu
1               5

<210> SEQ ID NO 3
<211> LENGTH: 9
<212> TYPE: PRT
<213> ORGANISM: Acinetobacter calcoaceticus

<400> SEQUENCE: 3

Ile Ser Arg Phe Ala Trp Gly Glu Val
1               5

<210> SEQ ID NO 4
<211> LENGTH: 9
<212> TYPE: PRT
<213> ORGANISM: Agrobacterium tumefaciens

<400> SEQUENCE: 4

Tyr Thr Arg Phe Thr Trp Gly Ala Pro
1               5

<210> SEQ ID NO 5
<211> LENGTH: 9
<212> TYPE: PRT
<213> ORGANISM: Ruminococcus albus

<400> SEQUENCE: 5

Tyr Thr Gln Phe Glu Ile Ser Ala Glu
1               5
```